United States Patent
Christian et al.

(10) Patent No.: US 11,583,597 B2
(45) Date of Patent: Feb. 21, 2023

(54) REDUCING MICROBIAL GROWTH ON FOOD PREPARATION, STORAGE, OR PROCESSING APPARATUS

(71) Applicant: Ecolab USA Inc., St. Paul, MN (US)

(72) Inventors: Paul Dominic Christian, Apple Valley, MN (US); Paul R. Kraus, Apple Valley, MN (US); Gina McDowell, Greensboro, NC (US); Amani Babekir, Greensboro, NC (US); Anna Starobin, Greensboro, NC (US)

(73) Assignee: Ecolab USA Inc., St. Paul, MN (US)

( * ) Notice: Subject to any disclaimer, the term of this patent is extended or adjusted under 35 U.S.C. 154(b) by 376 days.

(21) Appl. No.: 16/818,138

(22) Filed: Mar. 13, 2020

(65) Prior Publication Data

US 2020/0289683 A1 Sep. 17, 2020

Related U.S. Application Data

(60) Provisional application No. 62/819,028, filed on Mar. 15, 2019.

(51) Int. Cl.
*A61L 2/08* (2006.01)
*A23G 9/30* (2006.01)
(Continued)

(52) U.S. Cl.
CPC ............... *A61L 2/084* (2013.01); *A23G 9/30* (2013.01); *A47J 31/60* (2013.01); *A61L 2/24* (2013.01);
(Continued)

(58) Field of Classification Search
CPC .. A23G 9/30; A23G 9/305; A23L 2/50; A23L 3/00; A47J 31/60; A61L 2/08;
(Continued)

(56) References Cited

U.S. PATENT DOCUMENTS 5,755,103 A    5/1998   Na et al.
6,524,529 B1 *   2/2003   Horton, III ............. B65B 55/08
                                                  210/636
(Continued)

FOREIGN PATENT DOCUMENTS

CN      204121454 U    1/2015
CN      104704067 A    6/2015
(Continued)

OTHER PUBLICATIONS

International Preliminary Report on Patentability from International Application No. PCT/US2020/022594, dated Sep. 30, 2021, 10 pp.

(Continued)

*Primary Examiner* — Britt D Hanley
(74) *Attorney, Agent, or Firm* — Shumaker & Sieffert, P.A.

(57) ABSTRACT

A lighting array including one or more antimicrobial light segments configured to emit light sufficient to inactivate one or more microorganisms at a target surface may be installed within identified contamination zones of food or beverage preparation, processing, storing or packaging equipment or machinery. In an ice machine, for example, an array controller is configured for communication with an ice machine controller to receive ice machine status information signals. The status information signals are usable by the array controller to determine cycle, state, and/or usage information associated with the ice machine. The array controller may individually control activation of the one or more antimicrobial light segments based on the status information signals received from the machine controller to achieve inactivation of one or more microorganisms on target surfaces within the machine.

26 Claims, 6 Drawing Sheets

(51) Int. Cl.
*A47J 31/60* (2006.01)
*A61L 2/24* (2006.01)

(52) U.S. Cl.
CPC ........ *A61L 2202/11* (2013.01); *A61L 2202/14* (2013.01)

(58) Field of Classification Search
CPC ... A61L 2/084; A61L 2/10; A61L 2/24; A61L 2202/11; A61L 2202/14; F25C 1/00; F25C 2400/12
See application file for complete search history.

(56) References Cited

U.S. PATENT DOCUMENTS

| | | | |
|---|---|---|---|
| 6,573,663 | B1 | 6/2003 | MacGregor et al. |
| 7,270,195 | B2 | 9/2007 | MacGregor et al. |
| 8,182,744 | B2 | 5/2012 | Mlodzinski et al. |
| 8,398,264 | B2 | 3/2013 | Anderson et al. |
| 9,039,966 | B2 | 5/2015 | Anderson et al. |
| 9,700,641 | B2 | 7/2017 | Hawkins et al. |
| 9,839,706 | B2 | 12/2017 | Anderson et al. |
| 9,963,597 | B2 | 5/2018 | Aizenberg et al. |
| 2004/0175290 | A1 | 9/2004 | Scheir et al. |
| 2006/0021375 | A1 | 2/2006 | Wetzel et al. |
| 2010/0303671 | A1 | 12/2010 | Bertrand |
| 2012/0228645 | A1* | 9/2012 | Tu .................. F21K 9/00 257/E33.066 |
| 2013/0224086 | A1 | 8/2013 | Stibich et al. |
| 2014/0061509 | A1 | 3/2014 | Shur et al. |
| 2014/0079587 | A1 | 3/2014 | Dayton |
| 2016/0271803 | A1 | 9/2016 | Stewart |
| 2016/0375161 | A1 | 12/2016 | Hawkins et al. |
| 2017/0095585 | A1 | 4/2017 | Smetona et al. |
| 2017/0100989 | A1 | 4/2017 | Chapaton et al. |
| 2017/0246331 | A1 | 8/2017 | Lloyd |
| 2017/0340761 | A1* | 11/2017 | Shur .................. A61L 2/10 |
| 2017/0368213 | A1 | 12/2017 | Mintie et al. |
| 2018/0023821 | A1 | 1/2018 | Kim et al. |
| 2018/0046166 | A1 | 2/2018 | Kumar et al. |
| 2018/0117189 | A1 | 5/2018 | Yadav et al. |
| 2018/0117190 | A1 | 5/2018 | Bailey |
| 2018/0117193 | A1 | 5/2018 | Yadav et al. |
| 2018/0124883 | A1 | 5/2018 | Bailey |
| 2018/0126021 | A1 | 5/2018 | Valentine et al. |
| 2018/0154027 | A1 | 6/2018 | Anderson et al. |
| 2018/0243452 | A1 | 8/2018 | Hawkins et al. |
| 2018/0243453 | A1 | 8/2018 | Hawkins et al. |
| 2018/0345485 | A1 | 12/2018 | Sinnet et al. |
| 2019/0176338 | A1 | 6/2019 | Zito et al. |
| 2019/0298871 | A1 | 10/2019 | Dobrinsky |
| 2020/0205926 | A1 | 7/2020 | Keibel |

FOREIGN PATENT DOCUMENTS

| | | |
|---|---|---|
| CN | 204864170 U | 12/2015 |
| CN | 105856259 A | 8/2016 |
| CN | 105879148 A | 8/2016 |
| CN | 105963730 A | 9/2016 |
| CN | 205747250 U | 11/2016 |
| CN | 106272467 A | 1/2017 |
| CN | 206085069 U | 4/2017 |
| CN | 206795846 U | 12/2017 |
| CN | 108068125 A | 5/2018 |
| CN | 207710799 U | 8/2018 |
| CN | 108606754 A | 10/2018 |
| CN | 108714884 A | 10/2018 |
| CN | 109065186 A | 12/2018 |
| CN | 106444564 B | 1/2019 |
| CN | 109202939 A | 1/2019 |
| CN | 109276728 A | 1/2019 |
| CN | 109316612 A | 2/2019 |
| CN | 109431810 A | 3/2019 |
| CN | 109481707 A | 3/2019 |
| CN | 109481708 A | 3/2019 |
| DE | 102017209966 A1 | 12/2018 |
| EP | 3355940 A2 | 8/2018 |
| JP | 2015167470 A | 9/2015 |
| JP | 2018117586 A | 8/2018 |
| KR | 1499359 B1 | 3/2015 |
| KR | 1724447 B1 | 4/2017 |
| KR | 20180010824 A | 1/2018 |
| KR | 20190054955 A | 5/2019 |
| WO | 2003096387 A2 | 11/2003 |
| WO | 2006124211 A1 | 11/2006 |
| WO | 2014036080 A1 | 3/2014 |
| WO | 2017062260 A2 | 4/2017 |
| WO | 2018087171 A1 | 5/2018 |
| WO | 2018122009 A1 | 7/2018 |

OTHER PUBLICATIONS

U.S. Appl. No. 17/101,449, filed Nov. 23, 2020, by Finison.
U.S. Appl. No. 17/325,398, filed May 20, 2021, by Voss et al.
U.S. Appl. No. 17/325,440, filed May 20, 2021, by Hatch et al.
"Hubbell Lighting to Integrate Bacteria Suppressing Technology into Smart Luminaires," http://www.lightingdesignandspecification.ca/changing-scene/2322-hubbe, Jun. 1, 2018, 1 pp.
"Ice UV," retrieved from https://www.freshaireuv.com/ice-machines/ on Feb. 22, 2019, 5 pp.
"Light Fixture Kills Bacteria Safely, Continuously," Science Daily, Jun. 26, 2015, 2 pp.
"Hubbell Lighting Secures Licensing Agreement with the University of Strathclyde High Intensity Narrow Spectrum Technology," Hubbell Lighting, May 4, 2018, 3 pp.
Lacombe et al., "Reduction of Bacterial Pathogens and Potential Surrogates on the Surface of Almonds Using High-Intensity 405-nanometer light," Journal of Food Protection, vol. 79, No. 11, Nov. 2016, pp. 1840-1845.
Gunther et al., "The Effects of 405-nm Visible Light on the Survival of Campylobacter on Chicken Skin and Stainless Steel," Foodborne Pathogens and Disease, vol. 13, No. 5, May 2016, 6 pp.
Kim et al., "Antibacterial Effect and Mechanism of High-Intensity 405 ± 5 nm Light Emitting Diode on *Bacillus cereus*, *Listeria monocytogenes*, and *Staphylococcus aureus* Under Refrigerated Condition," Journal of Photochemistry and Photobiology B: Biology, vol. 153, Dec. 2015, pp. 33-39.
Murdoch et al., "Inactivation of Campylobacter jejuni by Exposure to High-Intensity 405-nm Visible Light," Foodborne Pathogens and Disease, vol. 7, No. 10, Oct. 2010, pp. 1211-1216.
Roh et al., "Blue Light-Emitting Diode Photoinactivation Inhibits Edwardsiellosis in Fancy Carp (*Cyprinus carpio*)," Aquaculture, vol. 483, Jan. 20, 2018, pp. 1-7.
Ramakrishnan et al., "Differential Sensitivity of Osteoblasts and Bacterial Pathogens to 405-nm Light Highlighting Potential for Decontamination Applications in Orthopedic Surgery," Journal of Biomedical Optics, vol. 9, No. 10, Oct. 2014, 8 pp.
McDonald et al., "405 nm Light Exposure of Osteoblasts and Inactivation of Bacterial Isolates from Arthroplasty Patients: Potential for New Disinfection Applications?", European Cells and Materials, vol. 25, Mar. 7, 2013, pp. 204-214.
MacLean et al., "Sporicidal Effects of High-Intensity 405 nm Visible Light on Endospore-Forming Bacteria," Photochemistry and Photobiology, vol. 89, No. 1, Jan./Feb. 2013, pp. 120-126.
Liang et al., "Blue Light Induced Free Radicals from Riboflavin on *E. coli* DNA Damage," Journal of Photochemistry and Photobiology B: Biology, vol. 119, Dec. 29, 2012, pp. 60-64.
Endarko et al., "High-Intensity 405 nm Light Inactivation of Listeria monocytogenes," Photochemistry and Photobiology, vol. 88, No. 5, Sep.-Oct. 2012, pp. 1280-1286.
Murdoch et al., "Bactericidal Effects of 405nm Light Exposure Demonstrated by Inactivation of *Escherichia*, *Salmonella*, *Shigella*, *Listeria*, and *Mycobacterium* Species in Liquid Suspensions and on Exposed Surfaces," The Scientific World Journal, vol. 2012, Apr. 1, 2012, 8 pp.
MacLean et al., "High-Intensity Narrow-Spectrum Light Inactivation and Wavelength Sensitivity of *Staphylococcus aureus*," Federation of European Microbiological Societies, Jun. 16, 2008, pp. 227-232.

(56) References Cited

OTHER PUBLICATIONS

Kingsley et al., "Evaluation of 405-nm Monochromatic Light for Inactivation of Tulane Virus on Blueberry Surfaces," Journal of Applied Microbiology, vol. 124, No. 4, Apr. 2018, pp. 1017-1022.
"LG Electronics LP153HD3B Installation Guide," retrieved from manualzz.com/doc/4030343/lg-electronics-lp153hd3b-installation-guide on May 11, 2020, 2 pp.
International Search Report and Written Opinion of International Application No. PCT/US2020/022594, dated Jul. 13, 2020, 19 pp.
"Single Color Outdoor Weatherproof LED Flexible Lightstrip Part No. WFLS-x," https://d114hh0cykhyb0.cloudfront.net/pdfs/WFLS-x.pdf, Apr. 21, 2014, 2 pp.
"Wireless LED 4 Channel EZ Dimmer Controller with Channel Pairing," https://www.superbrightleds.comjmoreinfojrgb-led-controllers/wireless-4-channelrgb-led-dimmer-receiver/3372/7141/#tab/Reviews, Jul. 17, 2018, 7 pp.
Response to Communication Pursuant to Rules 161(1) and 162 EPC dated Oct. 22, 2021, from counterpart European Application No. 20718885.5, filed Apr. 19, 2022, 11 pp.

\* cited by examiner

REDUCING MICROBIAL GROWTH ON FOOD PREPARATION, STORAGE, OR PROCESSING APPARATUS

This application claims the benefit of U.S. Provisional Application No. 62/819,028, titled, "REDUCING MICROBIAL GROWTH ON FOOD PREPARATION, STORAGE, OR PROCESSING APPARATUS," filed Mar. 15, 2019, the entire content of which is incorporated herein by reference.

TECHNICAL FIELD

The disclosure relates to systems and methods of reducing microbial growth on surfaces of food processing, preparation, storage, or packaging equipment.

BACKGROUND

During the processing, preparation, storage, and packaging of food and beverage products, the food or beverage product may encounter microorganisms which may make the food or beverage product unsuitable for consumption. The microorganisms may come from the food itself, the food contact surfaces, and/or the surrounding environment. The microorganisms can range from pathogenic microorganisms (e.g., *Listeria monocytogenes*, enterohemorrhagic *Escherichia coli*, *Salmonella*, and the like) to spoilage organisms that can affect the taste, color, and/or smell of the final food product (e.g., *Pseudomonas, Acinetobacter, Moraxella, Alcaligenes, Flavobacterium, Envinia*, and the like). Microorganisms can affect a wide variety of food and beverage products including meat, poultry, fish and shellfish, cheese, fruits and vegetables, pre-prepared foods, beverages, water, ice, etc. These microorganisms may not only affect the quality of the food or beverage; microbial growth may also be present in and on the associated food processing, preparation, storage, or packaging equipment. At certain levels, the presence of microorganisms on a food or beverage product, or on the associated equipment, may cause everything from a consumer's perception of a lower quality product, regulatory investigations and sanctions, to the spread of foodborne illnesses. Thorough and frequent sanitization of equipment is thus important to help reduce the growth of such microorganisms.

SUMMARY

In general, the disclosure is directed to systems and/or methods of reducing microbial growth in or on food or beverage preparation, storage, processing, or packing equipment. In some examples, the systems and/or methods may help reduce the frequency at which such equipment needs to be cleaned to keep the microbial growth below acceptable levels.

In one example, the disclosure is directed to a system comprising: a lighting array including one or more antimicrobial lighting segments, each antimicrobial lighting segment including one or more elements, wherein each element emits light at a wavelength and irradiance sufficient to inactivate one or more microorganisms on a target surface associated with a food machine; and a lighting array controller comprising: one or more processors; and a data storage device comprising instructions that when executed by the one or more processors cause the one or more processors to: receive one or more signals usable to determine status information concerning the food machine; and individually control each antimicrobial lighting segment based on the determined status information concerning the food machine.

In some examples, the status information concerning the food machine may include cycle information for the food machine. The food machine may include an ice machine, and the status information may include cycle information for the ice machine. The cycle information may include one of an ice making cycle, an ice harvesting cycle, or a standby cycle. The status information may include cycle information of the food machine, and the one or more processors may individually control each antimicrobial light segment based on the cycle information.

The one or more processors may individually control each antimicrobial light segment based on the determined status information by activating a first set of the antimicrobial lighting segments and deactivating a second set of the antimicrobial lighting segments. The determined status information may include a door open state, and the one or more processors may deactivate at least some of the antimicrobial lighting segments when the determined status information is indicative of a door open state. Each of the one or more antimicrobial lighting segments may be individually controllable such that each lighting segment may be activated at a first, high setting, a second, modified setting, or a third, deactivated setting independently of the other one or more antimicrobial lighting segments. The status information may include usage information indicative of whether the food machine is in a high use state or a low use state. The status information may include usage information indicative of whether the food machine is in a high use state or a low use state, and the one or more processors may activate all of the one or more antimicrobial lighting segments at a high setting upon determining that the food machine is in a high usage state.

The one or more antimicrobial lighting segments may be disposed within the food machine to direct light at the wavelength and irradiance sufficient to inactivate one or more microorganisms toward one or more target surfaces associated with the food machine. The food machine may include a plurality of target surfaces, and wherein the one or more antimicrobial lighting segments may be individually controllable to direct light at the wavelength and irradiance sufficient to inactivate one or more microorganisms at different target surfaces based on the determined status information.

Each antimicrobial lighting segment may include a substrate and a plurality of light-emitting diode (LED) elements, and each LED element may emit light including wavelengths in a range of about 405±10 nanometers. Each antimicrobial lighting segment may include a flexible substrate and a plurality of light-emitting diode (LED) elements, wherein each LED element emits light in a wavelength range of about 405±10 nanometers, and wherein a length of each antimicrobial lighting segment may be customized to fit within a target space within the food machine. In some examples, the wavelength range may be about 405±5 nanometers.

The lighting array and the lighting array controller may be connected to receive power from the food equipment. The lighting array and the lighting array controller may be connected to receive power from an external AC power source. The lighting array may further include one or more lighting elements that emit light having a wavelength range in the visible spectrum.

In another examples, the disclosure is directed to a method comprising: disposing a lighting array including one or more antimicrobial lighting segments, each antimicrobial lighting segment including one or more elements, wherein each element emits light at a wavelength and irradiance sufficient to inactivate one or more microorganisms on at least one target surface associated with the food machine; receiving one or more signals usable to determine status information concerning the food machine; and individually controlling each antimicrobial lighting segment based on the determined status information concerning the food machine.

The method may further include that each element emits light including wavelengths in a range of about 405±10 nanometers. The method may further include each element emits light including wavelengths in a range of about 405±5 nanometers. The method may further include that each element includes an LED that emits light including wavelengths in a range of about 405±5 nanometers.

The method may further include individually controlling each of the one or more antimicrobial lighting segments such that each antimicrobial lighting segment may be activated at a first, high setting, a second, modified setting, or a third, deactivated setting independently of the other one or more antimicrobial lighting segments.

The details of one or more examples are set forth in the accompanying drawings and the description below. Other features and advantages will be apparent from the description and drawings, and from the claims.

DETAILED DESCRIPTION

Figure 2:
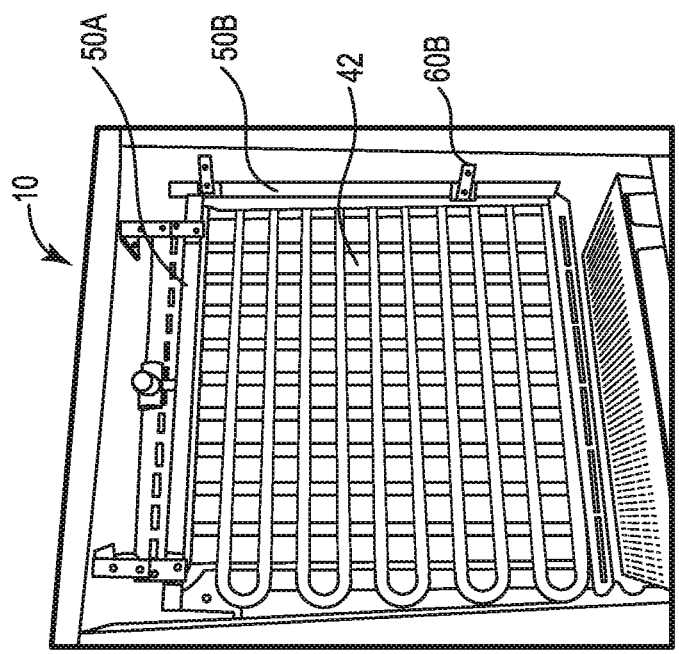
FIG. 2 is a photograph of an example ice machine evaporation compartment with two antimicrobial light segments installed for microbial inactivation on target surfaces in accordance with the present disclosure.

In general, the disclosure is directed to systems and/or methods of reducing microbial growth in or on food or beverage preparation, storage, processing, or packaging machinery and equipment. Such machinery and equipment will be referred to herein generally as food equipment or food machinery. In some examples, the systems and/or methods according to the present disclosure may help reduce the frequency in which such food equipment needs to be cleaned and/or sanitized to keep microbial growth below acceptable levels.

Light having wavelengths in a range of approximately 405±10 nanometers (nm) has been demonstrated to decontaminate the air and exposed surfaces by inactivating microorganisms and pathogens. The systems and methods in accordance with the present disclosure concern the strategic application and control of an antimicrobial lighting system within or on food equipment or machinery. Such food equipment may include, for example, refrigeration units, freezer units, cooling units, ice machines, ice dispensers, produce cases, food or beverage display or holding equipment, hot or cold beverage dispensers, blast chillers, food prep tables, kitchen appliances, dishwashers, and any other type of food processing, preparation, storage, or packaging equipment, machinery, and surfaces.

For purposes of the present disclosure, the term "antimicrobial light" will be used generally to refer to light including wavelengths in a range of 405±10 nm (i.e., from about 395-415 nm) and having sufficient irradiance (power received by a surface per unit area) of these wavelengths as measured at a target surface to result in inactivation of one or more microorganisms at the target surface within a desired period of time. In some examples, the antimicrobial light source(s) may include one or more light source elements, such as light-emitting diodes (LEDs), emitting wavelengths in a range of about 405±10 nm. It shall be understood that the particular range of wavelengths emitted by the element(s) of each antimicrobial lighting segment may vary somewhat from these stated ranges, depending, for example, on the response curve for each particular lighting element, and the disclosure is not limited in this respect. Also, each element does not necessarily emit light across the entire wavelength range. In general, the antimicrobial light contains at least some of these wavelengths at a sufficient intensity to affect inactivation of one or more microorganisms on a target surface.

In some examples, the antimicrobial light(s) may also include light of other wavelengths, such as visible light including wavelengths from about 380 to 740 nm. The intensity of the visible light may be sufficient for illumination when viewed by the human eye. The visible light and the antimicrobial light may be emitted from the same light source elements or from different light source elements.

An antimicrobial lighting system may include an array of one or more individually controllable antimicrobial light segments. Each antimicrobial light segment may include a substrate and one or more light emitting elements, such an LED light strip, wherein each of the light emitting elements emits light at a wavelength and irradiance sufficient to inactivate one or more microorganisms on a target surface. Other examples may include LED tube lights, light bars, rope lights, bulbs, individual light emitting elements, and any other flexible or inflexible light element configuration or shape. Each individual light element may be directional or omnidirectional. Individual control of the antimicrobial light segments may be based on cycle and/or usage information received from an associated piece of food equipment or machinery in which the antimicrobial light segments are installed. The light segments may be customized in size and shape to both fit within the desired spaces within or on the associated piece of food equipment or machinery, and to provide sufficient irradiance at one or more target surfaces within the machine to achieve a desired level of microbial inactivation at those surfaces, or to prevent microbial growth at those surfaces, within a desired period of time.

The one or more antimicrobial lighting segments may be disposed within the food machine to direct light at the wavelength and irradiance sufficient to inactivate one or more microorganisms toward one or more target surfaces associated with the food machine.

In an ice machine, for example, an antimicrobial lighting system may include an array of one or more individually controllable antimicrobial light segments positioned within the ice machine at identified zones or points of contamination risk, such as at or around the exterior of the distribution bar assembly (herein referred to as a distribution tube), inside of the distribution tube, above or within the water recirculation sump reservoir, around the exterior of or inside the riser tube, adjacent to the evaporator, at the source water inlet, in the ice collection bin, or any other identified risk area. A light array controller is connected to receive cycle data from an ice machine controller. Each identified contamination risk zone within the ice machine is illuminated with light of an antimicrobial wavelength at a sufficient dosage to effect microbial inactivation on identified target surfaces or zones within the machine. The dosage may be defined as the irradiance, or the power received by a surface per unit area (e.g., as measured in watts per square centimeter, $W/cm^2$) of the antimicrobial wavelength(s) measured at the target surface. The irradiance is dependent at least in part by the power applied to the light source, the distance from the light source to the surface, the total surface area illuminated, and the time of exposure.

In some examples, it is not necessary to illuminate all zones or surfaces within the machine continuously or at the same time or at the same dose. Zones can be treated automatically and selectively by the antimicrobial light when the treatment is most effective and/or based on the cycle of the machine process controller. In other words, for example, if the ice machine is in active ice making mode, target zones/surfaces may include the incoming water supply, the distribution tube and the evaporator. Other zones may not be simultaneously illuminated in order to reduce energy consumption and lengthen LED life. When ice making is off, antimicrobial light treatment zones may include the sump water reservoir and the ice collection bin, and these zones may be automatically activated, and other treatment zones may be optionally deactivated, based on status information signals received from the ice machine controller. This antimicrobial light treatment protocol may thus be driven in response to the ice machine's internal control logic controlling the ice making processes. The antimicrobial light treatment protocol may include a high exposure setting (full power on or highest intensity) antimicrobial cycle mode that occurs when the machine is not in normal use (at night, for example) as well as a treatment interrupt mode (power down) for power savings or to minimize exposure risk (for example, when a machine is being serviced). The antimicrobial light treatment protocol may also include a reduced power mode or modified setting in which certain antimicrobial light segments are selectively controlled to output a reduced intensity, but at a level that is sufficient to inactivate one or more microorganisms at the target surface(s).

The antimicrobial lighting systems may include lighting segments and/or lighting elements that output light at antimicrobial wavelengths alone or in combination with light of other wavelengths (e.g., one or more wavelengths of visible light). For example, some lighting segments or lighting elements may output antimicrobial light while other lighting segments or lighting elements output light within the visible spectrum. This may help provide illumination within or on the food equipment or machinery that is aesthetically pleasing to humans and/or to more closely represent true colors than illumination by antimicrobial wavelengths alone, which may appear blue to the human eye.

An antimicrobial light array may be installed in the ice machine in such a manner that there is overlapping illumination from each successive lighting element at the target surface at which microbial inactivation is desired. This cone of illumination illuminates a surface area dependent upon the design and physical arrangement of the individual light elements in each lighting segment and the distance of the element(s) from the target surface. The design and installation of the light array will be such that there is continuous or intermittent illumination at the surface throughout the target surface being treated. It shall be understood that the irradiance power at the surface being treated is dependent upon the distance between the emitter and the surface. The power of the antimicrobial light shall be controlled such that sufficient irradiance required for microbiological mitigation within the desired time period is achieved. It shall further be understood that the time/irradiance/distance power relationship required for microbiological mitigation depends upon the target organism(s).

LED lifetime of the antimicrobial lights can range from hundreds to in excess of 100,000 hours of operation. Furthermore, the emitted power of the lamp can be modulated using a Pulse-Width-Modulation (PWM) technique to achieve higher irradiant power without stressing the antimicrobial light to the extent that the light's lifetime is adversely affected when operated under constant power. The frequency and duty cycle applied to the antimicrobial light segments may be modulated to achieve the desired irradiance power at the target surface(s). PWM enables the color temperature (spectral distribution) of the LED lamp to be maintained while varying the observed lamp brightness.

In some examples, antimicrobial light segments may be fabricated from, for example, flexible LED light strips in which each LED light element is designed to emit wavelengths in the antimicrobial range of about 405±10 nm. Such antimicrobial light segments may be installed in a piece of food equipment or machinery to treat susceptible areas of internal water circuits, such as distribution headers & bars, water reservoirs, and riser tubes. In an ice machine, areas requiring antimicrobial treatment may include one or more of the ice bin walls (the compartment containing ice), inside of water distribution tube, water curtain, inside of water pump tube, water pan, inside surface of splash guard (front of machine, removable), reservoir wall (above water line), evaporation wall, interior top and side panels, water trough, water diverter, non-food contact areas, filters, and any other identified target zones or surfaces.

Target organisms that may be found in or on food equipment or machinery, and that may be inactivated using the antimicrobial lighting systems and methods of the present disclosure include, but are not limited to, bacteria, yeasts, and molds, such as *Bacillus* species, *Pseudomonas* species, *Yersinia enterocolitica, Listeria monocytogenes, Staphylococcus aureus, Salmonella species, E. coli,* coliforms, *Legionella* species, *Acinetobacter* species, *Candida* species, *Saccharomyces* species, *Aspergillus* species, *Moraxella, Alcaligenes, Flavobacterium, Erwinia*, and any other pathogen or microorganism that may be encountered in such environments.

Figure 1:
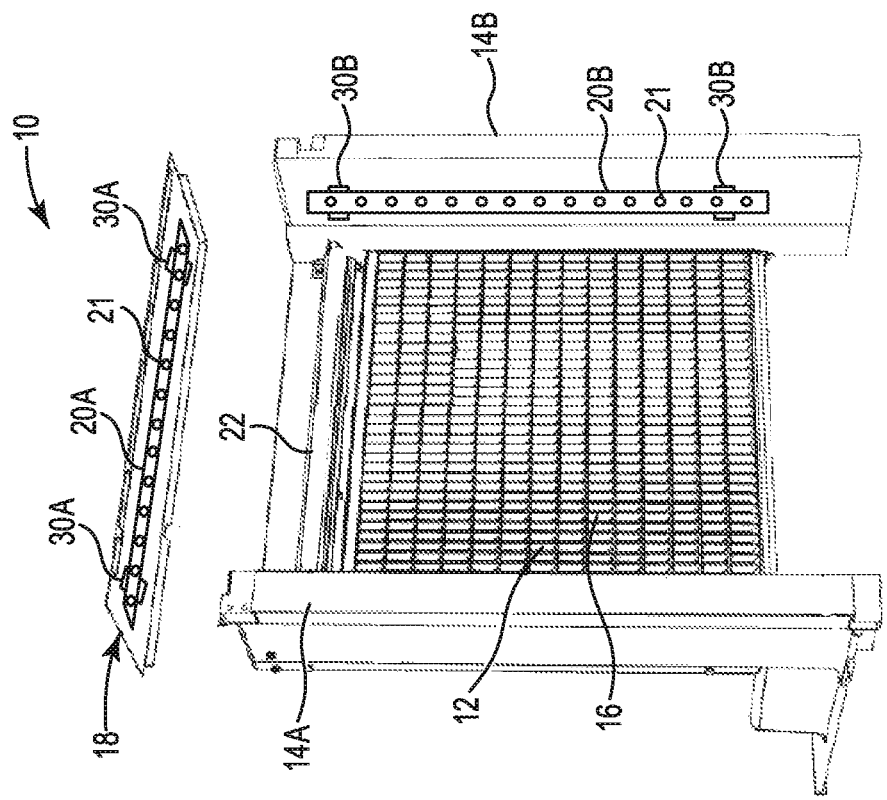
FIG. 1 shows an exploded schematic diagram of an example ice machine evaporation compartment with two antimicrobial light segments installed for microbial inactivation on target surfaces in accordance with the present disclosure.

As one example, FIG. 1 shows an exploded schematic diagram of an example ice machine evaporation compartment 10 with two antimicrobial light segments 20A and 20B installed for microbial inactivation at one or more target surfaces. FIG. 2 is a photograph of a similar ice machine evaporation compartment 40 having an evaporator 42 with two antimicrobial light segments 50A and 50B installed within the compartment similarly to the schematic of FIG. 1. Each light segment 20A and 20B, and 50A and 50B, includes one or more LEDs (such as LEDs 21 as indicated on FIG. 1). Each antimicrobial light segment 20A and 20B (and light segments 50A and 50B) may be individually controllable such that they may be activated and/or deactivated independently of one another.

In the example of FIG. 1, evaporation compartment 10 includes an evaporator 12, water distribution tube 22, side panels 22A and 22B, top panel 18, and bottom panel/trough 26. Trough 26 may serve to direct ice cubes dispensed from evaporator 12 to a storage bin. Antimicrobial light segments 20A and 20B are mounted to the top panel 18 and side panel 14B, respectively, and emit antimicrobial light at a wavelength and irradiance sufficient to inactivate one or more microorganisms at the target surface(s) within the evaporation compartment. For example, antimicrobial light segments 20A and 20B may include one or more elements that emit light at a wavelength of about 405±10 nm and at a sufficient irradiance to achieve sufficient levels of microorganism inactivate at the target surface(s). Additional antimicrobial light segments may also be mounted to side panel 14A and trough 26 to provide substantially complete antimicrobial illumination within the interior of the evaporation compartment. In this configuration, the antimicrobial light segments are able to illuminate and inactivate microorganisms at one or more target surfaces within the ice machine, including evaporator 12, water distribution tube 22, interior surfaces of top panel 18, side panels 14A and 14B, trough 26, the ice cubes themselves (indicated generally by reference numeral 16), and other interior features of evaporation compartment 10. Use of multiple customizable and individually controllable antimicrobial light segments allows for greater distribution and illumination of antimicrobial light to achieve microbial inactivation at almost any target surface associated with a food machine. For example, areas that may be shadowed from one antimicrobial light source by presence of parts within the machine may be illuminated by other antimicrobial light sources strategically placed in and around the interior and/or exterior of the machine such that shadowing within the machine can be minimized.

It shall be understood that other configurations of antimicrobial light arrays including one or more antimicrobial light segments may be adapted for installation in any other food equipment or machinery. For example, although the antimicrobial light segments of FIGS. 1 and 2 are shown as being straight line segments, an implementation using flexible LED light strips (or any other type of flexible lighting strip capable of emitting the desired antimicrobial wavelengths) enables each segment to be cut, bent or curved to fit almost any shaped or curved surface or space within or on almost any type of food equipment. In addition, multiple such flexible antimicrobial light segments may be assembled together in an array of individually controllable antimicrobial light segments to provide thorough antimicrobial light application to identified risk areas in or on a piece of food or beverage equipment. As another example, waterproof and flexible antimicrobial light segments may be placed inside water supply tubing, inside of storage bins or troughs, inside of the motor or generator compartment, in or over drainage trays or drainage lines, or any other location where growth of microorganisms is of concern.

Figure 3:
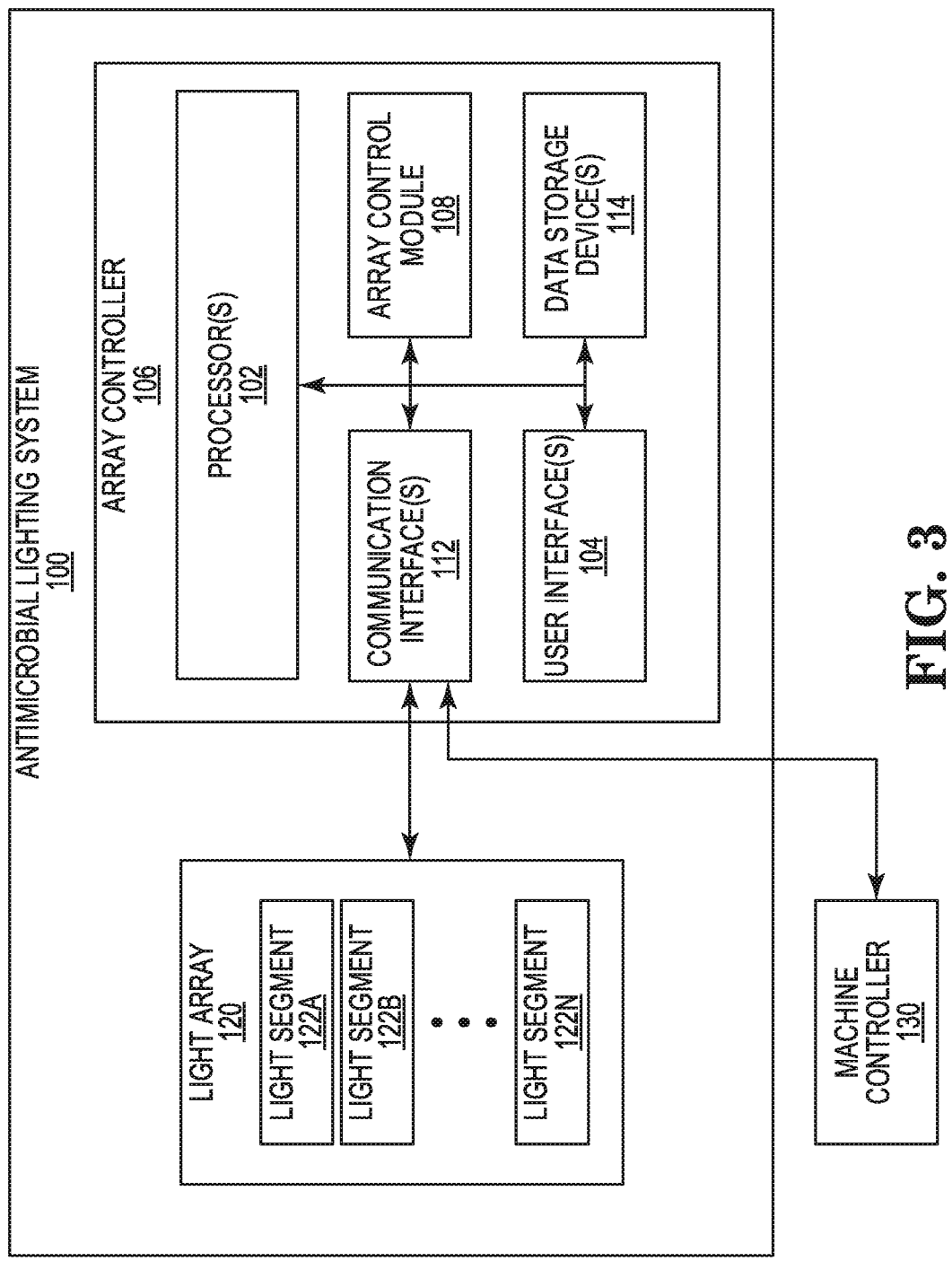
FIG. 3 is a block diagram illustrating an example antimicrobial lighting system including a light array, a light array controller and one or more individually controllable antimicrobial light segments in accordance with the present disclosure.

FIG. 3 is a block diagram illustrating an example antimicrobial lighting system 100. Antimicrobial lighting system 100 includes an array controller 106 and a light array 120 including one or more individually controllable antimicrobial light segments 122A-122N. In this example, array controller 106 is configured to communicate with an ice machine controller 130. In this way, array controller 106 receives machine status information, including cycle information, state information, and/or usage information from ice machine controller 130. The status information may be indicative of the current state or cycle of the associated ice machine. In the ice machine example, machine states may include ice bin door open or closed states, evaporator panel open or closed states, a machine on or off state, etc. Machine state information may further include information from one or more sensors associated with the machine including evaporator compartment temperature sensors, ice bin temperature sensors, water temperature sensors, door open/closed sensors, humidity sensors, vibration sensors, defrost sensors, ice thickness sensors, water fill activation, and any other sensor associated with the food equipment or machinery. The status information may also be indicative of an environmental state inside of the ice machine. For example, if the air space inside a machine compartment (e.g., the evaporator compartment or the ice bin compartment in the ice machine example) has become contaminated with particulates that can cause or lead to microbial contamination, and the condition can be detected or sensed, an antimicrobial lighting segment could be activated to remediate that condition. Additional sensor information may include environmental monitoring to indicate conditions of increased microbial activity, such as airborne yeast or mold or contaminated water supply. The detection of these conditions can indicate that the antimicrobial light power should be increased as a preventative measure against the increased microbial activity.

Machine cycles may include an ice making cycle, a harvest cycle, a preparation cycle, etc. The usage information may include information concerning the timing and/or frequency of one or more cycles or states of the machine, which may be indicative of the relative degree of usage of the machine. Although an ice machine controller 130 is shown and described for purposes of this example, it shall be understood that antimicrobial lighting system 100 may be configured to communicate with the controller of any other electronically controlled piece of food equipment or machinery, and the disclosure is not limited in this respect.

In some examples, each antimicrobial light segment 122A-122N may be implemented using a commercially available LED light strip having a peak wavelength of about 405±5 nm, such as the Single Color Outdoor Weatherproof LED Flexible Light Strip, wavelength 405 nm, Part Number WFLS-UV30, available from Super Bright LEDs Inc., of St. Louis, Mo., USA (www.superbrightleds.com). These segments are waterproof, flexible, and may be cut to desired lengths for each application, or to fit the intended space within the ice machine (or other food equipment or machinery). Each antimicrobial light segment 122A-122N may be adhered to a mounting fixture using an integrated adhesive strip. Each antimicrobial light segment 122A-122N may then be affixed to the desired location within the ice machine using a suitable adhesive or mounting hardware.

Array controller 106 is a computing device that includes one or more processors 102, an array control module 108, one or more user interface components 104, one or more communication components 112, and one or more data storage components 114. User interface components 104 may include one or more of audio interface(s), visual interface(s), and touch-based interface components, including a touch screen, display, speakers, buttons, keypad, stylus, mouse, or other mechanism that allows a person to interact with a computing device. In this example, communication components 112 are configured to communicate control signals from processors 102 to individually control antimicrobial light segments 122A-122N within antimicrobial lighting array 120. Communication components 112 are also configured to receive ice machine status information signals from ice machine controller and transmit the ice machine status information signals to processors 102. The ice machine status information signals are usable by the one or more processors to determine cycle, state, and/or usage information associated with the ice machine. In other examples, communication components 112 may also allow controller 106 to communicate with other remote or local computing devices via wired and/or wireless connections.

Array control module 108 includes computer readable instructions configured to be executed on the one or more processors 102 to enable controller 106 to individually control activation of antimicrobial light segments 122A-122N of light array 120. For example, array control module 108 may enable controller 100 to individually control activation of antimicrobial light segments 122A-122N based on the status information signals received from the ice machine controller (or status information signals from other food equipment). Processor(s) may analyze the received status information signal to determine a current cycle or state of the ice machine. For example, one or more of the antimicrobial light segments 122A-122N may be activated to emit antimicrobial light at a first, high setting (that is, highest intensity) during certain cycles of the ice machine. As another example, one or more of the antimicrobial light segments 122A-122N may be activated to emit antimicrobial light at a second, low setting (that is, relatively lower intensity than the high setting) during certain cycles of the ice machine. As another example, one or more of the antimicrobial light segments 122A-122N may be deactivated so as not to emit antimicrobial light, or be placed in an "off" setting, during certain cycles of the ice machine.

Array control module 108 may also enable controller 106 to individually control activation of antimicrobial light segments 122A-122N based on the time of day. For example, one or more of the antimicrobial light segments 122A-122N may be activated to emit antimicrobial light at a first, high setting (i.e., a highest intensity) during certain defined time periods of the day (e.g., at night or when a store or restaurant is closed, or at times of the day when the ice machine typically experiences high levels of usage, for example). As another example, one or more of the antimicrobial light segments 122A-122N may be activated to emit antimicrobial light at a second, low setting (that is, relatively lower intensity than the high setting) during certain defined time periods of the day. As another example, one or more of the antimicrobial light segments 122A-122N may be deactivated so as not to emit antimicrobial light, or be placed in an "off" setting, during certain defined time periods of the day.

In other examples, the antimicrobial light segments 122A-122N may be controlled by array controller 106 such that some of the antimicrobial light segments 122A-122N operate at a high setting, other of the antimicrobial light segments 122A-122N operate a lower setting (relatively lower than the high setting), and still other of the antimicrobial light segments 122A-122N are deactivated or turned off. It shall be understood, therefore, that each of the antimicrobial light segments 122A-122N may be individually controlled by array controller 106 to individually active/deactivate and/or adjust the power and/or intensity of the antimicrobial light output by each antimicrobial light segment 122A-122N, and thus to adjust the irradiance of the antimicrobial light received at the target surface(s).

Data storage devices 114 of array controller 106 include data received, used or generated by processors 102 during execution of the array control module 108 and/or other functionality of computing device 202. For example, storage components 114 may include any data or cycle signals received from ice machine controller 130, data entered by a user via user interface components 104, or data used or generated by array control module 108.

Antimicrobial lighting system 100 may include its own internal power supply (such as one or more batteries) or it may be powered appropriately from line power directly (e.g., AC power) or through one or more connections internal to the ice machine or other associated food equipment.

The status information signals received by array controller 106 from ice machine controller 130 are indicative of the current state or cycle of the ice machine. Ice machine cycles may include, for example, a preparation cycle, an ice making cycle, an ice harvest cycle, and an off/full cycle. During the ice making cycle, water flows from the water distribution tube 22 and across the evaporator. The evaporator is chilled, allowing ice to build up to a preset thickness. During the ice harvest cycle, excess water is drained, and the evaporator is warmed slightly to allow the sheets of cubed ice to slide down into trough 26, where they are directed into a storage bin. In a typical commercial application, an ice machine will continuously repeat the ice making/harvest cycles unless a bin full switch is tripped, or the machine is powered off. The bin full switch may be tripped when the ice machine has produced sufficient ice to fill the storage bin to a specified level, at which time the ice machine will shut down. When bin full switch is toggled again, indicating the ice level has dropped below the specified level, the ice machine starts a new ice making cycle.

Antimicrobial lighting system 100 (including array controller 106 and antimicrobial light segments 122A-122N) may be powered by an internal power source (e.g., one or more batteries) or it may be powered from external power (e.g., AC power) received from an external power source (not shown). Alternatively, antimicrobial lighting system 100 may be connected to receive power from ice machine controller 130 or from the ice machine, thus saving on outlet space.

Antimicrobial light segments 122A-122N may also include one or more LED drivers that are connected to array controller 106 through communication interface(s) 112, and which are configured to individually drive the antimicrobial light segments 122A-122N in response to commands received from array controller 106.

Array control module 108 may include instructions that enable array controller 106 to individually control antimicrobial light segments 122A-122N using one or more settings. For example, the settings may include a high or full power or level setting (e.g., a maximum voltage/current applied), which means that maximum power or level is applied to a selected one or more of the antimicrobial segments 122A-122N. The settings may also include one or more modified power or level settings, such as one or more dimmed settings (e.g., 50% of maximum power, 25% of maximum power, or other selected percentage(s)), which means that the modified power is applied to selected one or more of the antimicrobial light segments. The settings may also include a deactivated setting, in which one or more of the antimicrobial light segments 122A-122N are turned off.

The different level settings correspond to different levels of light output by the antimicrobial light segments 122A-122N. For example, a high or maximum setting corresponds to the highest light output of an antimicrobial light segment (however that maximum may be defined for the system design). A medium or modified setting corresponds to a reduced light output (reduced or lower relative to the high or maximum setting) of an antimicrobial light segment. An "off" setting corresponds to no light output. The medium or modified settings do not necessarily correspond in a linear relationship with the voltage applied to an antimicrobial light segment, as the response curve of the antimicrobial lights are not necessarily linear with respect to the applied voltage. In other words, a 50% power applied (compared to a maximum power) does not necessarily result in 50% of maximum light output if the response of the antimicrobial light in questions is not linear. However, it shall be understood that reduced settings correspond to reduced power or voltage applied, and a reduced light output by the affected antimicrobial light segments.

The antimicrobial light segments 122A-122N are individually controllable by array controller 106 such that they are not all necessarily driven at the same setting(s) at the same time(s). Thus, at any given time, a first selected set of one or more antimicrobial light segment(s) 122A-122N may be driven at first, high, setting, a second selected set of one or more antimicrobial light segment(s) 122A-122N may be driven at a second, modified, setting, and a third selected set of one or more antimicrobial light segment(s) 122A-122N may be deactivated or off.

Control of the setting(s) may be received by array controller 106 from user interface 104 in response to inputs from a user. For example, through the user interface 104, a user may input the desired settings (e.g., high, modified, off, etc.) for some or all of the antimicrobial light segments 122A-122N. Control of the setting(s) may also be determined based on ice machine cycle signals received from the ice machine controller 130, ice machine usage signals from the ice machine controller 130. For example, array control module 108 may analyze the ice machine cycle signals received form the ice machine controller 130 and/or the ice machine usage signals received from the ice machine controller 130 to individually control activation of selected antimicrobial light segments 122A-122N at the appropriate setting(s) based on the analysis.

For example, if the ice machine cycle signal received from the ice machine controller indicates that the ice machine is in ice making mode or harvest mode, array controller 106 may activate one or more of antimicrobial light segments 122A-122N at a modified (reduced) power setting. As another example, if the ice machine cycle signal indicates that the ice machine has not been in use for a defined period of time, array controller 106 may determine that the ice machine is not currently being heavily used and may activate one or more of antimicrobial light segments 122A-122N at a highest setting for maximum decontamination of the target surfaces of the ice machine.

As another example, if the ice machine usage signals received from the ice machine controller 130 indicates that the ice machine is currently experiencing heavy usage, array controller 106 may reduce the power or deactivate selected ones of the antimicrobial light segments 122A-122N. If the ice machine usage signals indicate that the ice machine is current experience reduced levels of usage (or no usage), array controller 106 may activate selected ones (or all) of the antimicrobial light segments 122A-122N for maximum decontamination of the target surfaces of the ice machine.

Control of the settings may also be determined based on the time of day. For example, array control module 108 may determine the time and date to determine whether the current time corresponds to a heavy usage time of the ice machine or to a reduced or standby usage time of the ice machine. In a restaurant application, for example, a heavy usage time for an ice machine may correspond to the hours around mealtimes, such as breakfast, lunch, and/or dinner, while a reduced usage time may correspond to nighttime hours when the restaurant is closed. The frequency of accessing the ice bin, as determined by a bin door interlock switch, can indicate increased usage thereby increasing antimicrobial light array power. Array control module 108 may there determine the time and date and individually control activation of selected antimicrobial light segments 122A-122N based on the time and date. For example, array control module 108 may activate all antimicrobial light segments 122A-122N at a maximum setting upon determining that the time and date correspond to a time when the ice machine typically experiences a reduced or no usage level (such as when a restaurant is closed). Array control module 108 may activate selected antimicrobial light segments 122A-122N at a reduced setting (e.g., a lower power or off setting) upon determining that the time and date correspond to a time when the ice machine typically experiences maximum usage levels.

Figure 4:
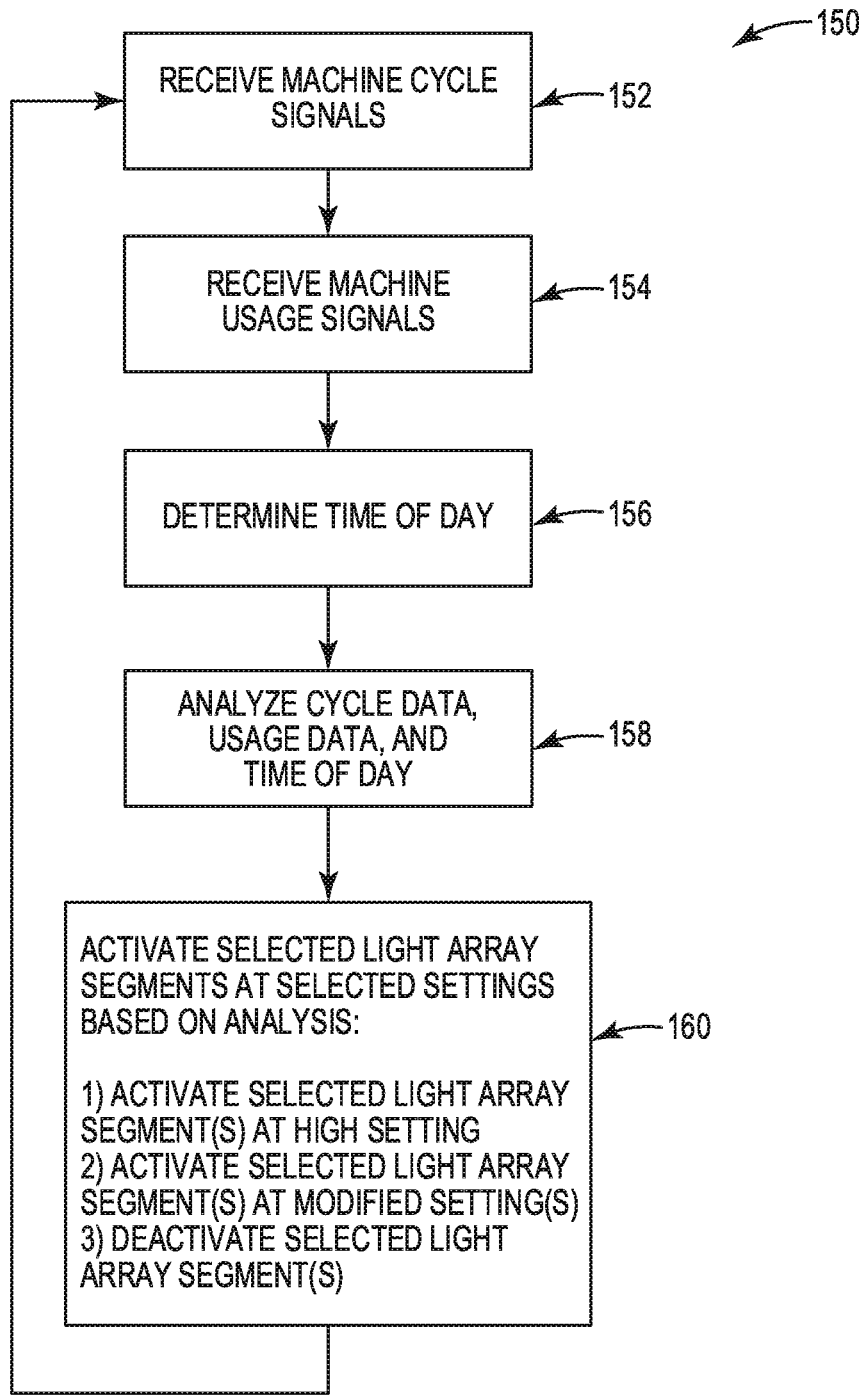
FIG. 4 is a flowchart illustrating an example process by which an array controller may individually control one or more antimicrobial light segments in accordance with the present disclosure.

FIG. 4 is a flowchart illustrating an example process 150 by which a computing device (such as array controller 106 of FIG. 3) may individually control one or more antimicrobial light segments (such as antimicrobial light segments 122A-122N of FIG. 3) in accordance with the present disclosure. Process (150) will be described with respect application and control of antimicrobial light to achieve microbial inactivation at one or more target surfaces associated with an electronically controlled piece of food equipment or machinery; however, it shall be understood that process (150) may apply to application and control of antimicrobial light for microbial inactivation at one or more target surfaces within or any type of food equipment or machinery, and that the disclosure is not limited in this respect. In other words, the process (150) may receive or determine machine cycle and usage information in some other way, such as by tapping into the machine's fan or motor actuation signals, electronically controlled valve signals, receiving information from external temperature or cycle sensors, receiving a door open/closed signal from a door interlock switch, etc.

In the example of FIG. 4, a computing device (such as array controller 106 of FIG. 3) receives ice machine cycle signal(s) from an ice machine controller (152). The ice machine cycle signal(s) include information indicative of the current state or cycle of the associated ice machine. The ice machine cycles may include, for example, an ice making cycle, an ice harvesting cycle, a standby cycle, a preparation cycle, and an ice machine off cycle. The ice machine states may include, for example, a machine on/off state, an ice bin door open/closed state, an evaporator panel open/closed state, one or more malfunction states, and the like.

The computing device may also receive ice machine usage signal(s) from the ice machine controller (154). The ice machine usage signals include information indicative of the current or historical usage level(s) experienced by the ice machine. For example, the ice machine may be experiencing a high level of usage (e.g., a predefined number of ice making cycles completed in a specified period of time), a reduced level of usage (e.g., relatively less than a high level of usage), may be inactive (e.g., has not completed an ice making cycle for a predetermined period of time), or it may be turned off. The ice machine usage signals may further include historical information concerning operation of the ice machine over a period of time, such as dates, cycle on/off times, cycle lengths, evaporator and/or water temperatures, number of cycles per unit time, indications of when the ice bin door was open or closed, indications of when the evaporator panel was removed or reinstalled, indications of one or more malfunctions and the time and date stamp associated with those malfunctions, etc.

The computing device may also determine the current time and date (156). The time and date may be indicative of high, reduced, or inactive levels of usage. For example, in a restaurant application, the hours surrounding meal times such as breakfast, lunch, or dinner may be associated with relatively higher levels of usage than other times, such as between meal times or when the restaurant is closed, for example.

The computing device analyzes the ice machine cycle signals, the ice machine usage signals, and/or the current time and date information to determine how to individually control each of the antimicrobial light segments (158). For example, the computing device may determine that some or all of the antimicrobial light segments should be activated at the high or maximum setting; the computing device may determine that some or all of the antimicrobial light segments should be activated at a modified or reduce setting(s); and/or the computing device may determine that some or all of the antimicrobial light segments should be deactivated (160).

As one example, the computing device may analyze the ice machine cycle signals and determine that the ice bin compartment door is open. In response to determining that the ice bin compartment door is open, the computing device may deactivate the antimicrobial light segments installed in the ice bin compartment. Similarly, if the computing device analyzes the ice machine signals and determines that the bin compartment door has been subsequently closed, the computing device may activate the antimicrobial light segments in the ice bin compartment in response to determining that the ice bin compartment door has been closed. Activation of the water inlet solenoid valve would indicate water draw leading to increased need to power the antimicrobial light segments responsible for irradiating the water sump as a preventative measure.

Figure 5A:
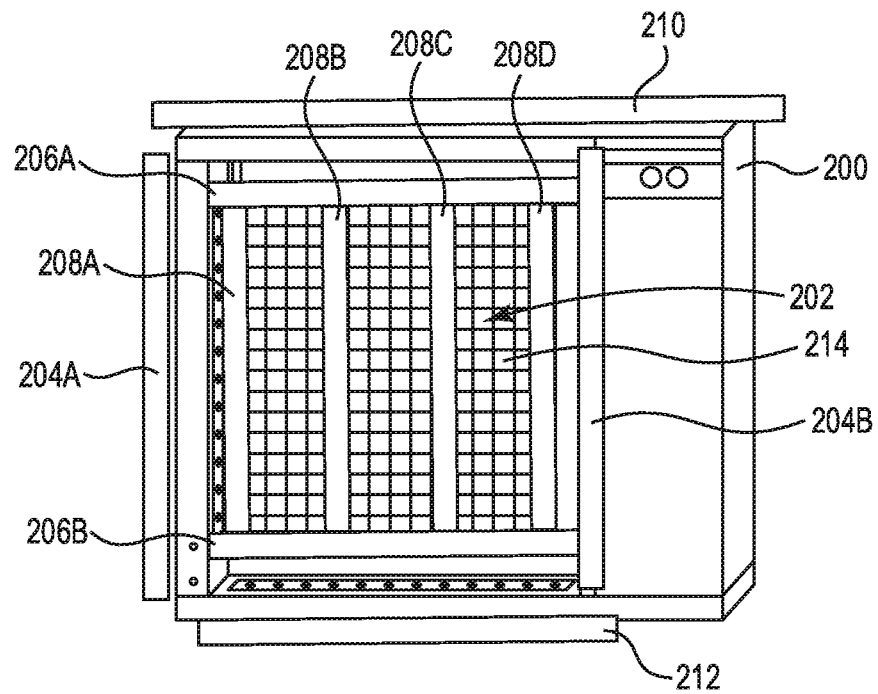
FIGS. 5A and 5B are front perspective and top views, respectively, of an example ice machine evaporation compartment and showing example locations for installation of antimicrobial light segments in the evaporation compartment.
Figure 5B:
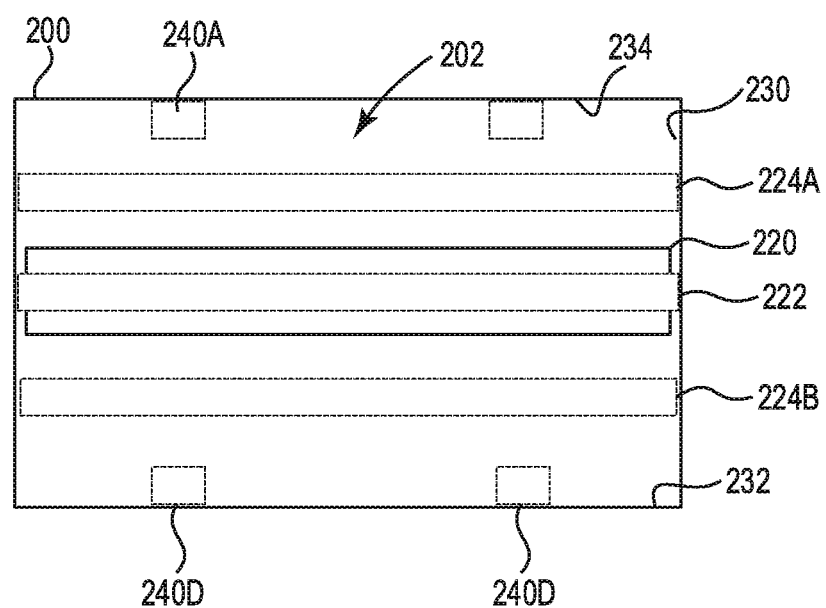

FIGS. 5A and 5B are front perspective and top views, respectively, of an example ice machine 200 and showing example locations for installation of antimicrobial light segments in the evaporation compartment 202. In this example, antimicrobial light segments 204A and 204B are mounted on the interior sidewalls of evaporator compartment 202; antimicrobial light segments 206A and 206B are mounted horizontally near the top and bottom, respectively, of the evaporator 214; antimicrobial light segments 208A-208D are mounted vertically on a back wall of evaporator compartment 202; antimicrobial light segment 210 is mounted on top of the top panel of the ice machine 200; antimicrobial light segment 212 is mounted on the bottom panel of the ice machine 200.

FIG. 5B shows antimicrobial light segments 224A and 224B mounted on the interior of the front and back panels 232 and 234, respectively, of the distribution bar 220. Antimicrobial light segment 222 is located directly above distribution bar 220. Antimicrobial light segments 240A-240D are mounted vertically on the front and back panels of the evaporator compartment 202. Some or other of the antimicrobial light segments may be disposed within the evaporation compartment, or within other target spaces within an ice machine, to direct antimicrobial light at the water curtain covering the ice-forming surface. Other locations associated with an ice machine where antimicrobial light segments may be installed may include any target area or surface within, on, or outside an ice machine at which inactivation of microorganisms may be desirable.

Figure 6:
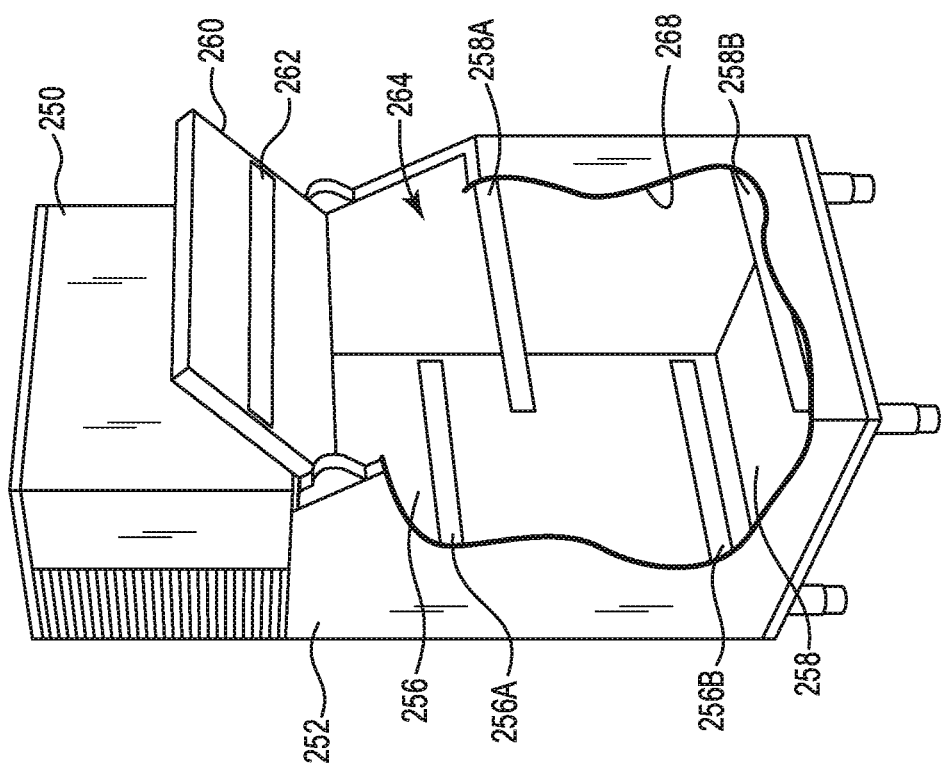
FIG. 6 is a front perspective view of an example ice machine and ice storage compartment and showing example locations for installation of antimicrobial light segments in the ice storage compartment.

FIG. 6 is a front perspective view of an example ice machine 250 and ice storage bin 252 and showing example locations for installation of antimicrobial light segments inside of the ice storage compartment 264. In this example, antimicrobial light segments 256A and 256B are installed on the interior side of a back panel 256 of the ice compartment; antimicrobial light segments 258A and 258B are installed on the interior side of a front panel 268 of the ice compartment. Antimicrobial light segment 262 is installed on an interior side of ice compartment door 260. Installation of antimicrobial light segments throughout the ice compartment in this manner helps to ensure that all target surfaces within the ice compartment are illuminated with antimicrobial light of sufficient intensity to achieve sufficient inactivation of microorganisms on the target surfaces within the compartment.

Figure 7:
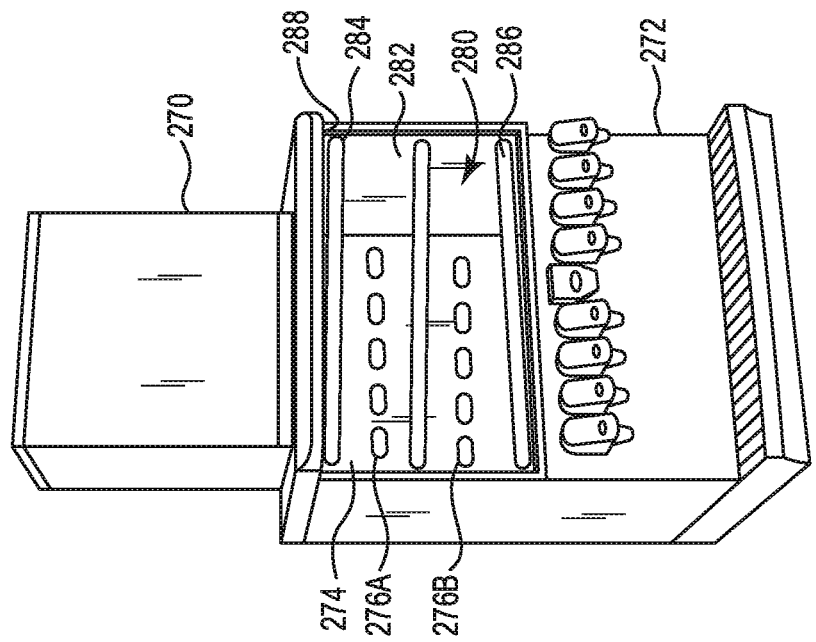
FIG. 7 is a front perspective view of an example ice/beverage dispenser, including an ice machine and an ice storage compartment and showing example locations for installation of antimicrobial light segments in the ice storage compartment.

FIG. 7 is a front perspective view of an example ice machine 270 and an ice/beverage dispenser 272 with the front panel of an ice storage compartment removed. FIG. 7 shows example locations for installation of antimicrobial light segments within ice storage compartment 280. In this example, antimicrobial light segment 284 is installed/mounted on an interior side of top panel 288; antimicrobial light segment 286 and 288 are mounted on an interior side of a front panel (not shown) of the ice storage compartment; and antimicrobial light segments 276A and 276B are mounted on an interior side of back panel 274. Other antimicrobial light segments may also be disposed within one or more target areas of the ice machine and/or ice/beverage dispenser so as to inactivate one or more microorganisms at one or more target surfaces within or on the machines. Installation of antimicrobial light segments throughout the ice storage compartment in this manner helps to ensure that all target surfaces within the ice storage compartment are illuminated with antimicrobial light of sufficient irradiance to achieve sufficient inactivation of microorganisms on the target surfaces within the compartment.

EXAMPLES

Lab experiments to evaluate the antimicrobial effect of antimicrobial lights in an ice machine environment were performed.

Test Materials

Antimicrobial LED Lights (405 nm wavelength)

Media: Tryptic Soy Agar and Sabouraud Dextrose Agar

Phosphate Buffered Dilution Water (PBDW)

Test organisms:
- Pseudomonas fluorescens (ATCC 13525)
- Escherichia coli (ATCC 11229)
- Saccharomyces cerevisiae (ATCC 834)
- Candida albicans (ATCC 10231)

Text Fixture Configuration

Figure 8:
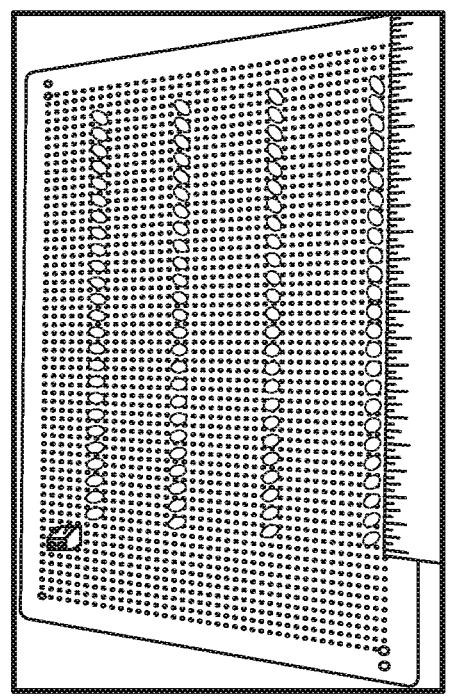
FIG. 8 is a photograph of an antimicrobial light lamp test fixture used to evaluate the antimicrobial effect of antimicrobial lights in an ice machine.

An antimicrobial lamp test fixture (FIG. 8) was assembled by creating a lamp fixture comprised an array of LEDs that emit light at 405 nm were selected as the antimicrobial light. The array of Bivar UV3TZ-405-30 LEDs was assembled in 4 rows of 23 LEDs using 120 Ω resistors to limit the LED current to 15 mA at 5VDC. The maximum recommended current for these LEDs is 20 mA and previous experience with these LEDs has shown that the lamp intensity will decrease in time when driven at the maximum current to yield the maximum intensity.

The spacing of the rows of lamps was selected so that each row is located above the centerline of the wells of a 12-well culture plate.

Figure 9:
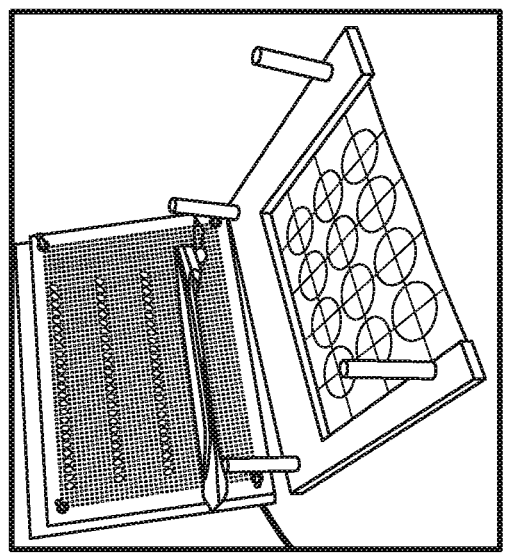
FIG. 9 is a photograph of the antimicrobial light lamp test fixture of FIG. 8 mounted on an assembly that positioned the well plate below the lamps.

The test fixture was mounted on an assembly that positioned the well plate properly below the lamps, as shown in FIG. 9.

The fourth row of lamps was covered to provide uniform illumination of each of the three rows of wells in the plate.

Figure 10:
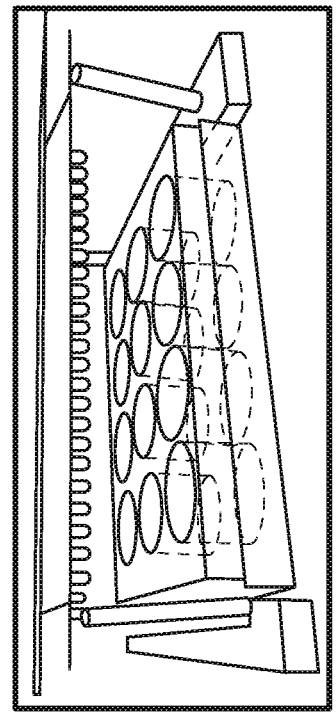
FIG. 10 is a photograph of the antimicrobial light lamp test fixture of FIGS. 8 and 9 assembled such that that each row of lamps is located above the centerline of the wells of a 12-well culture plate.

When assembled, the lamps were located 1.75" above the bottom of the wells, as shown in FIG. 10.

The irradiance at 405 nm was measured at each of the 12 well locations using a Gentec Pronto-Si laser power meter. The measured power for each of the 12 locations are:

|  | Gentec (mW · cm$^{-2}$) | | | |
|---|---|---|---|---|
| back left | 15.0 | 14.2 | 16.0 | 15.0 |
|  | 14.0 | 15.2 | 15.6 | 11.7 |
|  | 13.3 | 14.5 | 14.6 | 13.7 | front right |

The average power across the array was 14.4±1.1 mW·cm$^{-2}$. Based on this average power the energy impinging on the sample wells over time was used to calculate antimicrobial light exposure in the sample wells.

| t/min | J · cm$^{-2}$ Gentec |
|---|---|
| 10 | 8.6 |
| 20 | 17.3 |
| 30 | 25.9 |
| 45 | 38.9 |
| 60 | 51.8 |
| 65 | 56.2 |
| 90 | 77.8 |
| 120 | 103.7 |

Test System

Each test organism was transferred daily in broth media at least three times prior to the test.

Test Parameters

| Organisms |
|---|
| Pseudomonas fluorescens |
| E. coli |
| Saccharomyces cerevisiae |
| Candida albicans |

Test Procedure

1. Volume of 2 ml of bacterial suspension (10$^5$ CFU/mL) was transferred to each well of a 12-well multidish, which also contained a 7 mm 2 mm magnetic follower.

2. The 12-well multidish was placed under light source on a magnetic stirrer as per the specified distance and dose at the room temperature.

3. Samples of 0.1 ml were collected from the 12-well multidish at 10, 20, 30 minutes then hourly for up to 3 hours period and after 24 hours.

4. A control 12-well multidish were concurrently processed following a similar procedure without exposure to the light source.

5. Appropriate ten-fold or hundred-fold dilutions were prepared form the collected samples using PBDW. A single 0.1 mL aliquot of the dilution was spread plated using Tryptic Soy Agar for bacteria and Sabouraud Dextrose Agar for fungi.

6. The test was conducted in 2 replicates for each organism.

7. The test was repeated without stirring the bacterial suspension during the test.

Results of evaluating/understanding the efficacy of antimicrobial light in liquid media using most common organisms in an ice machine environment (Pseudomonas fluorescens, E. coli, Saccharomyces cerevisiae, Candida albicans) are shown in the following tables:

| Test (antimicrobial test fixture/Liquid media) | | Log (CFU) Survivors/ml | | | | | |
|---|---|---|---|---|---|---|---|
| Tested Organisms | Replicate | After 30 m | After 1 h | After 2 h | After 4 h | After 6 h | After 24 h |
| E. coli | R1 | 4.78 | 4.63 | 3.82 | 2.95 | 2.87 | 0.00 |
| E. coli | R2 | 4.80 | 4.54 | 3.99 | 3.15 | 2.76 | 0.00 |
| P. fluorescens | R1 | 3.34 | 2.48 | 0.00 | 0.00 | 0.00 | 0.00 |
| P. fluorescens | R2 | 3.08 | 1.00 | 0.00 | 0.00 | 0.00 | 0.00 |
| C. albicans | R1 | 4.72 | 4.84 | 3.84 | 2.92 | 2.79 | 0.30 |
| C. albicans | R2 | 4.83 | 4.84 | 3.88 | 2.86 | 2.64 | 0.00 |
| S. cerevisiae | R1 | 4.51 | 4.51 | 4.05 | 3.52 | 3.40 | 0.00 |
| S. cerevisiae | R2 | 4.61 | 4.58 | 3.91 | 3.60 | 3.32 | 0.00 |

| Control (no light/Liquid media) | | Log (CFU) Survivors/ml | | | | | |
|---|---|---|---|---|---|---|---|
| Tested Organisms | Replicate | After 30 m | After 1 h | After 2 h | After 4 h | After 6 h | After 24 h |
| E. coli | R1 | 5.00 | 4.97 | 5.09 | 5.02 | 5.17 | 5.98 |
| E. coli | R2 | 5.02 | 5.06 | 4.81 | 5.11 | 5.12 | 5.94 |
| P. fluorescens | R1 | 4.85 | 4.82 | 4.92 | 5.04 | 5.11 | 5.10 |
| P. fluorescens | R2 | 4.83 | 4.83 | 4.89 | 5.14 | 5.01 | 5.28 |
| C. albicans | R1 | 4.75 | 4.61 | 4.67 | 4.95 | 4.92 | 5.84 |
| C. albicans | R2 | 4.73 | 4.82 | 4.77 | 4.94 | 4.88 | 5.85 |
| S. cerevisiae | R1 | 4.88 | 4.75 | 4.83 | 4.88 | 4.85 | 5.08 |
| S. cerevisiae | R2 | 4.90 | 4.72 | 4.81 | 4.90 | 4.91 | 4.76 |

Results of evaluating the efficacy of antimicrobial light on a dried surface (stainless steel coupon) using most common organisms in ice machine environment (*Pseudomonas fluorescens, E. coli, Candida albicans*) are shown in the following tables:

| Test (antimicrobial test fixture/Stainless steel coupon) | | | | | |
|---|---|---|---|---|---|
| Tested Organisms | Replicate | Log (CFU) Survivors/Carrier | | | |
| | | After 5.5 h | After 24 h | After 48 h | After 72 h |
| E. coli | R 1 | 5.88 | 1.40 | 1.40 | 1.40 |
| E. coli | R2 | 5.60 | 1.40 | 1.40 | 1.40 |
| P. fluorescens | R 1 | 4.98 | 3.92 | 1.40 | 1.40 |
| P. fluorescens | R2 | 5.48 | 1.40 | 1.40 | 1.40 |
| C. albicans | R 1 | 4.74 | 2.85 | 1.40 | 1.40 |
| C. albicans | R2 | 4.17 | 3.90 | 1.40 | 1.40 |

| Control (no light/Stainless steel coupon) | | | | | |
|---|---|---|---|---|---|
| Tested Organisms | Replicate | Log (CFU) Survivors/Carrier | | | |
| | | After 5.5 h | After 24 h | After 48 h | After 72 h |
| E. coli | R 1 | 7.27 | 7.28 | 6.94 | 6.43 |
| E. coli | R2 | 7.27 | 7.30 | 6.99 | 6.28 |
| P. fluorescens | R 1 | 6.93 | 7.14 | 7.16 | 6.02 |
| P. fluorescens | R2 | 7.02 | 7.15 | 6.69 | 6.29 |
| C. albicans | R 1 | 5.45 | 5.42 | 5.12 | 4.24 |
| C. albicans | R2 | 5.08 | 5.32 | 5.05 | 5.00 |

Result Discussion

Liquid Media Test Result showed a complete reduction of bacteria and yeast residues in liquid media (from 5 log to zero log) within 24 hours of exposure to antimicrobial light compared to the control result.

Stainless Steel Coupons Test Result showed a complete reduction of bacteria and yeast residues on hard surfaces (from 5 log to 1 log–minimum detectable limit) within 48 hours of exposure to antimicrobial light compared to the control result.

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

In one or more examples, the functions described may be implemented in hardware, software, firmware, or any combination thereof. If implemented in software, the functions may be stored on or transmitted over as one or more instructions or code on a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium.

For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transitory media, but are instead directed to non-transitory, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable gate arrays (FPGAs), or other equivalent integrated or discrete logic circuitry. Accordingly, the terms "processor" and "processing circuitry" as used herein may refer to any of the foregoing structures or any other structure suitable for implementation of the techniques described herein. In addition, in some aspects, the functionality described herein may be provided within dedicated hardware and/or software modules configured for encoding and decoding, or incorporated in a combined codec. Also, the techniques could be fully implemented in one or more circuits or logic elements.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a codec hardware unit or provided by a collection of interoperative hardware units, including one or more processors as described above, in conjunction with suitable software and/or firmware.

ADDITIONAL EXAMPLES

Example 1

A system comprising: a lighting array including one or more antimicrobial lighting segments, each antimicrobial lighting segment including one or more elements, wherein each element emits light at a wavelength and irradiance sufficient to inactivate one or more microorganisms on a target surface associated with a food machine; and a lighting array controller comprising: one or more processors; and a data storage device comprising instructions that when executed by the one or more processors cause the one or more processors to: receive one or more signals usable to determine status information concerning the food machine; and individually control each antimicrobial lighting segment based on the determined status information concerning the food machine.

Example 2

The system of Example 1 wherein the status information concerning the food machine includes cycle information for the food machine.

Example 3

The system of Example 1 wherein the food machine is an ice machine, and wherein the status information includes cycle information for the ice machine.

Example 4

The system of Example 3 wherein the cycle information includes one of an ice making cycle, an ice harvesting cycle, or a standby cycle.

Example 5

The system of Example 1 wherein the status information includes cycle information of the food machine, and wherein the one or more processors individually control each antimicrobial light segment based on the cycle information.

Example 6

The system of Example 1 wherein the one or more processors individually control each antimicrobial light segment based on the determined status information by activating a first set of the antimicrobial lighting segments and deactivating a second set of the antimicrobial lighting segments.

Example 7

The system of Example 1 wherein the determined status information includes a door open state, and wherein the one or more processors deactivate at least some of the antimicrobial lighting segments when the determined status information is indicative of a door open state.

Example 8

The system of Example 1 wherein each of the one or more antimicrobial lighting segments are individually controllable such that each lighting segment may be activated at a first, high setting, a second, modified setting, or a third, deactivated setting independently of the other one or more antimicrobial lighting segments.

Example 9

The system of Example 1 wherein the status information includes usage information indicative of whether the food machine is in a high use state or a low use state.

Example 10

The system of Example 1 wherein the status information includes usage information indicative of whether the food machine is in a high use state or a low use state, and wherein the one or more processors activate all of the one or more antimicrobial lighting segments at a high setting upon determining that the food machine is in a high usage state.

Example 11

The system of Example 1 wherein the one or more antimicrobial lighting segments are disposed within the food machine to direct light at the wavelength and irradiance sufficient to inactivate one or more microorganisms toward one or more target surfaces associated with the food machine.

Example 12

The system of Example 1 wherein the food machine includes a plurality of target surfaces, and wherein the one or more antimicrobial lighting segments are individually controllable to direct light at the wavelength and irradiance sufficient to inactivate one or more microorganisms at different target surfaces based on the determined status information.

Example 13

The system of Example 1 wherein each antimicrobial lighting segment includes a substrate and a plurality of light-emitting diode (LED) elements, and wherein each LED element emits light including wavelengths in a range of about 405±10 nanometers.

Example 14

The system of Example 1 wherein each antimicrobial lighting segment includes a flexible substrate and a plurality of light-emitting diode (LED) elements, wherein each LED element emits light including wavelengths in a range of about 405±10 nanometers, and wherein a length of each antimicrobial lighting segment may be customized to fit within a target space within the food machine.

Example 15

The system of Example 1 wherein the lighting array and the lighting array controller are connected to receive power from the food equipment.

Example 16

The system of Example 1 wherein the lighting array controller and the lighting array are connected to receive power from an external AC power source.

Example 17

The system of Example 1 wherein the lighting array further includes one or more lighting elements that emit light having a wavelength range in the visible spectrum.

Example 18

A method comprising: disposing a lighting array including one or more antimicrobial lighting segments, each antimicrobial lighting segment including one or more elements, wherein each element emits light at a wavelength and irradiance sufficient to inactivate one or more microorganisms on at least one target surface associated with the food machine; receiving one or more signals usable to determine status information concerning the food machine; and individually controlling each antimicrobial lighting segment based on the determined status information concerning the food machine.

Example 19

The method of Example 18 wherein each element emits light including wavelengths in a range of about 405±10 nanometers.

Example 20

The method of Example 18 wherein each element emits light including wavelengths in a range of about 405±5 nanometers.

Example 21

The method of Example 18 wherein each element includes an LED that emits light including wavelengths in a range of about 405±5 nanometers.

Example 22

The method of Example 18 further including individually controlling each of the one or more antimicrobial lighting segments such that each antimicrobial lighting segment may be activated at a first, high setting, a second, modified setting, or a third, deactivated setting independently of the other one or more antimicrobial lighting segments.

Various examples have been described. These and other examples are within the scope of the following claims.

The invention claimed is:

1. A system comprising:
a lighting array including one or more antimicrobial lighting segments, each antimicrobial lighting segment including one or more elements, wherein each element of the one or more elements emits light at a wavelength and irradiance sufficient to inactivate one or more microorganisms on a target surface associated with a food machine; and
a lighting array controller comprising:
one or more processors; and
a data storage device comprising instructions that when executed by the one or more processors cause the one or more processors to:
receive, from a food machine, usage information indicative of a number of food machine cycles completed by the food machine in a specified period of time;
determine the food machine is in one of a first, high usage state or a second, reduced usage state based on the number of food machine cycles completed by the food machine in the specified period of time; and
individually control each of the one or more antimicrobial lighting segments based on determining the food machine is in one of the first, high usage state or the second, reduced usage state.

2. The system of claim 1, wherein the food machine is an ice machine, and wherein the usage information is indicative of a number of ice making cycles completed by the ice machine in the specified period of time.

3. The system of claim 2, wherein the ice making cycles include at least one of an ice making cycle, an ice harvesting cycle, or a standby cycle.

4. The system of claim 1, wherein the data storage device further comprises instructions that when executed by the one or more processors cause the one or more processors to:

receive food machine cycle information from a controller of the food machine indicative of a current cycle of the food machine, wherein the one or more antimicrobial lighting segments include a first antimicrobial lighting segment and a second antimicrobial lighting segment, and the one or more processors individually control each of the first and second antimicrobial lighting segments based on the food machine cycle information such that when the food machine is in a first food machine cycle at least the first antimicrobial lighting segments is activated to inactivate one or more microorganisms on a first target surface associated with the food machine, and when the food machine is in a second food machine cycle at least the second antimicrobial lighting segment is activated to inactivate one or more microorganisms on a second, different target surface associated with the food machine.

5. The system of claim 1, wherein the data storage device further comprises instructions that when executed by the one or more processors cause the one or more processors to:

receive food machine cycle information from a controller of the food machine indicative of a current cycle of the food machine, wherein the one or more antimicrobial lighting segments include a first set of the antimicrobial lighting segments and a second set of the antimicrobial lighting segments and the one or more processors individually control each of the first and second sets of the antimicrobial light segments based on the food machine cycle information by activating the first set of the antimicrobial lighting segments and deactivating the second set of the antimicrobial lighting segments.

6. The system of claim 1, wherein the data storage device further comprises instructions that when executed by the one or more processors cause the one or more processors to:

receive status information indicative of one of a door open state or a door closed state; and deactivate at least some of the antimicrobial lighting segments when the status information is indicative of the door open state.

7. The system of claim 1, wherein the one or more antimicrobial lightning segments includes a plurality of antimicrobial lighting segments, and each antimicrobial lighting segment of the plurality of antimicrobial lighting segments is individually controllable such that each of the antimicrobial lighting segments may be activated at a first, high setting, a second, modified setting, or a third, deactivated setting independently of the other one or more antimicrobial lighting segments.

8. The system of claim 1, wherein the data storage device further comprises instructions that when executed by the one or more processors cause the one or more processors to:

activate at least one of the one or more antimicrobial lighting segments at a high setting upon determining that the food machine is in the second, reduced usage state.

9. The system of claim 1, wherein the data storage device further comprises instructions that when executed by the one or more processors cause the one or more processors to:

activate all of the one or more antimicrobial lighting segments at a high setting upon determining that the food machine is in the first, high usage state.

10. The system of claim 1, wherein the one or more antimicrobial lighting segments are disposed within the food machine to direct light at the wavelength and irradiance sufficient to inactivate one or more microorganisms toward one or more target surfaces associated with the food machine.

11. The system of claim 1, wherein the food machine includes a plurality of target surfaces, and wherein the one or more antimicrobial lighting segments are individually controllable to direct light at the wavelength and irradiance sufficient to inactivate one or more microorganisms at different target surfaces of the plurality of target surfaces based on the usage information.

12. The system of claim 1, wherein each antimicrobial lighting segment of the one or more antimicrobial lighting segments includes a substrate, wherein the one or more elements include a plurality of light-emitting diode (LED) elements, and wherein each LED element of the plurality of LED elements emits light including wavelengths in a range of about 405±10 nanometers.

13. The system of claim 1, wherein each antimicrobial lighting segment of the one or more antimicrobial lighting segments includes a flexible substrate, wherein the one or more elements include a plurality of light-emitting diode (LED) elements, wherein each LED element of the plurality of LED elements emits light including wavelengths in a range of about 405±10 nanometers, and wherein a length of each antimicrobial lighting segment of the one or more antimicrobial lighting elements is customizable to fit within a target space within the food machine.

14. The system of claim 1, wherein the lighting array and the lighting array controller are connected to receive power from the food machine.

15. The system of claim 1, wherein the lighting array controller and the lighting array are connected to receive power from an external AC power source.

16. The system of claim 1, wherein the lighting array further includes one or more lighting elements that emit light having a wavelength range in the visible spectrum.

17. A method comprising:

disposing a lighting array including one or more antimicrobial lighting segments, each antimicrobial lighting segment including one or more elements, wherein each element of the one or more elements emits light at a wavelength and irradiance sufficient to inactivate one or more microorganisms on at least one target surface associated with a food machine;

receiving, by one or more processors, usage information indicative of a number of food machine cycles completed by the food machine in a specified period of time;

determining the food machine is in one of a first, high usage state or a second, reduced usage state based on the number of food machine cycles completed by the food machine in the specified period of time; and individually controlling each of the one or more antimicrobial lighting segments based on determining the food machine is in one of the first, high usage state or the second, reduced usage state.

18. The method of claim 17, wherein each of the elements emits light including wavelengths in a range of about 405±10 nanometers.

19. The method of claim 17, wherein each of the elements emits light including wavelengths in a range of about 405±5 nanometers.

20. The method of claim 17, wherein each of the elements includes an LED that emits light including wavelengths in a range of about 405±5 nanometers.

21. The method of claim 17, wherein the one or more antimicrobial lightning segments includes a plurality of antimicrobial lighting segments, the method further including individually controlling each antimicrobial lighting segment of the plurality of antimicrobial lighting segments such that each of the antimicrobial lighting segments may be activated at a first, high setting, a second, modified setting, or a third, deactivated setting independently of the other one or more antimicrobial lighting segments.

22. A non-transitory computer-readable storage medium comprising instructions that when executed by one or more processors cause the one or more processors to:
   receive usage information indicative of a number of food machine cycles completed by a food machine in a specified period of time;
   determine the food machine is in one of a first, high usage state or a second, reduced usage state based on the number of food machine cycles completed by the food machine in the specified period of time; and
   individually control each antimicrobial lighting segment of a lighting array comprised of a plurality of antimicrobial lighting segments to emit light at a wavelength and irradiance sufficient to inactivate one or more microorganisms on at least one target surface associated with the food machine based on determining the food machine is in one of the first, high usage state or the second, reduced usage state.

23. The non-transitory computer-readable medium of claim 22, wherein each antimicrobial lighting segment of the plurality of antimicrobial lighting segments includes one or more elements, and wherein each element of the one or more elements emits light including wavelengths in a range of about 405±10 nanometers.

24. The non-transitory computer-readable medium of claim 22, wherein each antimicrobial lighting segment of the plurality of antimicrobial lighting segments includes one or more elements, and wherein each element of the one or more elements includes an LED that emits light including wavelengths in a range of about 405±5 nanometers.

25. The non-transitory computer-readable medium of claim 22, wherein the one or more antimicrobial lightning segments includes a plurality of antimicrobial lighting segments, and wherein the non-transitory computer-readable medium further comprises instructions that when executed by one or more processors cause the one or more processors to:
   individually control each antimicrobial lighting segment of the plurality of the plurality of antimicrobial lighting segments such that each of the antimicrobial lighting segments may be activated at a first, high setting, a second, modified setting, or a third, deactivated setting independently of the other one or more antimicrobial lighting segments.

26. The system of claim 1, wherein the one or more antimicrobial lightning segments includes a plurality of antimicrobial lighting segments, and wherein the non-transitory computer-readable medium further comprises instructions that when executed by the one or more processors cause the one or more processors to:
   individually control each antimicrobial lighting segment of the plurality of antimicrobial lighting segments based on the usage information such that when the food machine is in the first, high usage state, at least one of the plurality of antimicrobial lighting segments is activated at a first, high setting, and when the food machine is in the second, reduced usage state, at least one of the plurality of antimicrobial lighting segments is activated at a second, modified setting.

* * * * *